(12) United States Patent
Kaneko

(10) Patent No.: US 12,340,079 B2
(45) Date of Patent: Jun. 24, 2025

(54) INTERPRETATION SUPPORT SERVER, INTERPRETATION SUPPORT SYSTEM, INTERPRETATION SUPPORT METHOD, INTERPRETATION SUPPORT PROGRAM, AND INTERPRETATION TERMINAL

(71) Applicant: FUJIFILM Corporation, Tokyo (JP)

(72) Inventor: Yasuhiko Kaneko, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 187 days.

(21) Appl. No.: 18/455,531

(22) Filed: Aug. 24, 2023

(65) Prior Publication Data

US 2023/0400974 A1    Dec. 14, 2023

Related U.S. Application Data

(63) Continuation of application No. PCT/JP2022/007785, filed on Feb. 25, 2022.

(30) Foreign Application Priority Data

Feb. 26, 2021   (JP) .................................. 2021-031132

(51) Int. Cl.
*G06F 3/04845*   (2022.01)
*G06F 3/14*      (2006.01)
(Continued)

(52) U.S. Cl.
CPC ............ *G06F 3/04845* (2013.01); *G06F 3/14* (2013.01); *G06T 3/40* (2013.01); *G06T 3/60* (2013.01); *G06T 7/0002* (2013.01)

(58) Field of Classification Search
CPC ......... G06F 3/04845; G06F 3/14; G06T 3/40; G06T 3/60; G06T 7/0002; G06T 7/00;
(Continued)

(56) References Cited

U.S. PATENT DOCUMENTS

2004/0120580 A1   6/2004  Sabol et al.
2012/0284606 A1   11/2012 Sitrick et al.
(Continued)

FOREIGN PATENT DOCUMENTS

JP    2002342485 A  *  11/2002
JP    2004-199691 A     7/2004
(Continued)

OTHER PUBLICATIONS

The extended European search report issued by the European Patent Office on Jun. 27, 2024, which corresponds to European Patent Application No. 22759779.6-1218 and is related to U.S. Appl. No. 18/455,531.

(Continued)

*Primary Examiner* — Jeffery A Brier
(74) *Attorney, Agent, or Firm* — Studebaker Brackett PLLC

(57) ABSTRACT

One embodiment of the present invention provides an interpretation support server, an interpretation support system, an interpretation support method, an interpretation support program, and an interpretation terminal that enable a plurality of users to efficiently perform interpretation. The interpretation support server according to one aspect of the present invention classifies an operation received from a first terminal into a display operation that permits display of an operation result on a second terminal and a hide operation that prohibits display of the operation result on the second terminal, causes the second terminal to display a result of performed display operation in real time in a case where the display operation is performed at the first terminal, and prohibits the second terminal from displaying a result of performed hide operation in a case where the hide operation is performed at the first terminal.

12 Claims, 12 Drawing Sheets

(51) Int. Cl.
*G06T 3/40* (2024.01)
*G06T 3/60* (2024.01)
*G06T 7/00* (2017.01)

(58) Field of Classification Search
CPC ...... G06Q 10/101; G06Q 10/20; G16H 30/40; G16H 50/20; G16H 50/30
See application file for complete search history.

(56) References Cited

U.S. PATENT DOCUMENTS

| | | |
|---|---|---|
| 2019/0170659 A1 | 6/2019 | Kaneko |
| 2019/0392943 A1 | 12/2019 | Sorenson et al. |
| 2020/0211692 A1 | 7/2020 | Kalafut et al. |
| 2021/0082114 A1 | 3/2021 | Harada |

FOREIGN PATENT DOCUMENTS

| | | |
|---|---|---|
| JP | 2018-180797 A | 11/2018 |
| WO | 2018/034057 A1 | 2/2018 |
| WO | 2019/230807 A1 | 12/2019 |

OTHER PUBLICATIONS

International Search Report issued in PCT/JP2022/007785; mailed May 17, 2022.
International Preliminary Report on Patentability (Chapter I) and Written Opinion of the International Searching Authority issued in PCT/JP2022/007785; issued Aug. 29, 2023.
Hirabayashi, Katsumi et al.; Mammography / Ultrasonic Diagnostic Equipment: Siemens Breast Imaging Solution; A Monthly Journal of Medical Imaging and Information; Nov. 1, 2017; vol. 49; No. 12; pp. 53-57.

* cited by examiner

INTERPRETATION SUPPORT SERVER, INTERPRETATION SUPPORT SYSTEM, INTERPRETATION SUPPORT METHOD, INTERPRETATION SUPPORT PROGRAM, AND INTERPRETATION TERMINAL

CROSS-REFERENCE TO RELATED APPLICATIONS

The present application is a Continuation of PCT International Application No. PCT/JP2022/007785 filed on Feb. 25, 2022 claiming priority under 35 U.S.C. § 119(a) to Japanese Patent Application No. 2021-031132 filed on Feb. 26, 2021. Each of the above applications is hereby expressly incorporated by reference, in its entirety, into the present application.

BACKGROUND OF THE INVENTION

1. Field of the Invention

The present invention relates to a technique for supporting interpretation of an object.

2. Description of the Related Art

In various fields, so-called "interpretation" (a user's inspection or diagnosis of an object using an image) is performed, and a technique for supporting this interpretation is known. For example, WO2018/034057A describes a technique for supporting inspection of a defect using an image of an industrial product on which inspection is to be performed. In addition, JP2004-199691A describes a technique of collating interpretation results of medical images by a plurality of users.

SUMMARY OF THE INVENTION

Interpretation may be difficult even for an experienced user depending on the situation, and defects, deformations, lesions, and the like may be overlooked. Therefore, a plurality of users may perform interpretation on the same image. However, in a case where a plurality of users interpret images separately and then collate the results, each user cannot refer to the interpretation results of other users, and it takes a long time until all the interpretations are finished. Further, image processing and image display conditions for interpretation may differ depending on the purpose of interpretation, the properties of an object, and users, and it is necessary to consider such circumstances in order for a plurality of users to perform efficient interpretation. However, such circumstances have not been taken into consideration in the related arts such as those disclosed in WO2018/034057A and JP2004-199691A described above.

In this way, it has been difficult for a plurality of users to efficiently perform interpretation with the related arts.

The present invention has been made in view of such circumstances, and an object of the present invention is to provide an interpretation support server, an interpretation support system, an interpretation support method, an interpretation support program, and an interpretation terminal that enable a plurality of users to efficiently perform interpretation.

In order to achieve the above-described object, there is provided an interpretation support server according to a first aspect of the present invention, the interpretation support server comprising a processor, in which the processor is configured to execute: image display processing for causing a first terminal connected to the interpretation support server and a second terminal different from the first terminal to display an image to be interpreted for an object; operation reception processing for receiving operations performed on the displayed image to be interpreted at the first terminal and the second terminal; own terminal result display processing for causing the first terminal to display a result of processing based on the operation received from the first terminal in real time and causing the second terminal to display a result of processing based on the operation received from the second terminal in real time; classification processing for classifying the operation received from the first terminal into a display operation and a hide operation; and other terminal result display processing for causing the second terminal to display a result of performed display operation in real time in a case where the display operation is performed at the first terminal, and prohibiting the second terminal from displaying a result of performed hide operation in a case where the hide operation is performed at the first terminal.

The interpretation support server according to the first aspect can classify, as a "display operation", an operation for which a result has to be transmitted to all other users, and classify, as a "hide operation", an operation for which settings are different for each user and an operation for which a result need not be transmitted to all other users, regarding an operation at the first terminal (a terminal used by a certain user) among the plurality of terminals (the first terminal and the second terminal).

Since the interpretation support server causes the second terminal (a terminal used by another user) to display the result of the display operation in real time according to the classification result, a user can grasp the result of the display operation by another user in real time. In addition, since the interpretation support server prohibits the second terminal from displaying the result of the hide operation, other users (users of the second terminal) do not have to see unnecessary processing results and the like.

In this way, with the interpretation support server according to the first aspect, a plurality of users can efficiently perform interpretation. Note that, in the first aspect and each of the following aspects, terminals with different users, terminals in which display is performed independently, and terminals (which may have the same hardware configuration and software configuration) that can be recognized as separate devices by the interpretation support server can be recognized as a "first terminal" and a "second terminal that is different from the first terminal". That is, the "first terminal" and the "second terminal" can be regarded as a "specific terminal" and a "terminal other than the specific terminal", and each interpretation terminal can be regarded as either a first terminal or a second terminal depending on whether or not it has received a specific operation.

In addition, in the first aspect and each of the following aspects, "real time" means that a response is quick, such as instant or immediate, and also includes cases where unavoidable time delays occur due to processing at the first and second terminals or the interpretation support server, or communication between these devices.

According to a second aspect, in the interpretation support server according to the first aspect, the processor is configured to, in the classification processing: classify, as the display operation, an operation in which users of the first terminal and the second terminal input information indicating an interpretation result of the image to be interpreted; and classify, as the hide operation, an operation in which the user of the first terminal inputs information regarding processing of the image to be interpreted. According to the second aspect, by classifying an operation of inputting information indicating an interpretation result as a "display operation" and causing the second terminal to display a result thereof, one user can easily grasp an interpretation result of another user, and a likelihood of errors in interpretation or oversights can be reduced. In addition, the interpretation support server classifies an operation of inputting information regarding processing of the image to be interpreted as a "hide operation" and prohibits the second terminal from displaying the operation result.

According to a third aspect, in the interpretation support server according to the second aspect, the processor is configured to, in the classification processing: receive, as the information indicating the interpretation result, at least one of the number, position, type, degree, or reason for determining the degree of defects in the image to be interpreted; and receive, as the information regarding processing of the image to be interpreted, at least one of an enlarging or reducing operation, a moving operation, a rotating operation, a transforming operation, an operation of changing a gradation, an operation of setting an interpretation range, an operation of designating a defect, or an operation of setting interpretation content for the image to be interpreted. The third aspect further specifically defines the display operation and the hide operation, and by receiving information such as the number and positions of defects as "information indicating an interpretation result" and classifying it as a "display operation", an advantageous effect such as prevention of oversight of defects is achieved. In addition, since appropriate conditions for operations such as enlarging the image to be interpreted differ depending on the user, by receiving such an operation as "information regarding processing" and classifying it as a "hide operation", each user can perform interpretation under desired conditions.

In addition, in the third aspect, in place of the defect or in addition to the defect, information about damage, deformation, a lesion, or a "region of interest" which is a candidate for the damage, the deformation, or the lesion may be received as "information indicating an interpretation result" and "information regarding processing of an image to be interpreted".

According to a fourth aspect, in the interpretation support server according to the third aspect, the processor is configured to: in the classification processing, receive, as the information regarding processing of the image to be interpreted, the operation of setting the interpretation range for the image to be interpreted; and perform notification processing for notifying a user of a confirmation result as to whether or not a region in which the object is shown in the image to be interpreted is entirely covered by the set interpretation range. In addition, in the fourth aspect, the interpretation support server can notify of the confirmation result using screen display, voice, or the like.

According to a fifth aspect, in the interpretation support server according to any one of the second to fourth aspects, the processor is configured to, in the other terminal result display processing, cause the second terminal to identify and display the information indicating the interpretation result in association with a fact that the interpretation result has been input from the first terminal. In addition, in the fifth aspect, for example, the interpretation support server can perform the identification display using characters, numbers, symbols, figures, or the like that are different for each user, and the color of the identification display may be changed for each user.

According to a sixth aspect, in the interpretation support server according to any one of the first to fifth aspects, the processor is configured to: in the operation reception processing, receive designation of a third terminal, the third terminal being different from the first terminal and the second terminal and being permitted to display a result of the hide operation: in the image display processing, cause the third terminal to display the image to be interpreted; and in the other terminal result display processing, cause the third terminal to display the result of the hide operation in real time. According to the sixth aspect, the result of the hide operation can be shared between the user of the first terminal and the user of the third terminal. Note that the processor can determine whether or not a certain terminal is the third terminal based on the designation of the user of the first terminal.

According to a seventh aspect, in the interpretation support server according to any one of the first to sixth aspects, the processor is configured to: in the operation reception processing, receive designation of a fourth terminal, the fourth terminal being different from the first terminal and the second terminal and being permitted to display a result of a specific hide operation which is a designated operation among the hide operations; in the image display processing, cause the fourth terminal to display the image to be interpreted; and in the other terminal result display processing, cause the fourth terminal to display the result of the specific hide operation in real time. According to the seventh aspect, the result of the hide operation can be shared between the user of the first terminal and the user of the fourth terminal. Note that the processor can determine whether or not a certain terminal is the fourth terminal based on the designation of the user of the first terminal.

According to an eighth aspect, in the interpretation support server according to any one of the first to seventh aspects, the processor is configured to cause the first terminal and the second terminal to display, as the image to be interpreted, any one of an image of a building, an image of an industrial product, or a medical image of a living body. The eighth aspect specifically defines the image to be interpreted.

In addition, in the eighth aspect, an image obtained by combining the individual images in a panoramic manner may be used as the image to be interpreted. An image is often divided and captured depending on the shape and size of the object, in such a case, a plurality of users may share and interpret a wide range. In such a case, the use of the combined image achieves the advantageous effect of the present invention that "a plurality of users can efficiently perform interpretation by preventing oversight, sharing a work range, and the like".

In order to achieve the above-described object, there is provided an interpretation support system according to a ninth aspect of the present invention, the interpretation support system comprising: an interpretation support server including a processor; a first terminal that is connected to the interpretation support server and displays an image to be interpreted; and a second terminal that is connected to the interpretation support server and displays the image to be interpreted, the second terminal being different from the first terminal, in which the processor is configured to execute: image display processing for causing the first terminal connected to the interpretation support server and the second terminal different from the first terminal to display the image to be interpreted for an object; operation reception processing for receiving operations performed on the displayed image to be interpreted at the first terminal and the second terminal; own terminal result display processing for causing the first terminal to display a result of processing based on the operation received from the first terminal in real time and causing the second terminal to display a result of processing based on the operation received from the second terminal in real time; classification processing for classifying the operation received from the first terminal into a display operation and a hide operation; and other terminal result display processing for causing the second terminal to display a result of performed display operation in real time in a case where the display operation is performed at the first terminal, and prohibiting the second terminal from displaying a result of performed hide operation in a case where the hide operation is performed at the first terminal. According to the ninth aspect, a plurality of users can efficiently perform the interpretation, similarly to the first aspect. In the interpretation support system according to the ninth aspect, the interpretation support server may have the same configuration as those of the second to eighth aspects.

In order to achieve the above-described object, there is provided an interpretation support method according to a tenth aspect of the present invention, the interpretation support method executed by an interpretation support server comprising: an image display step of causing a first terminal connected to the interpretation support server and a second terminal different from the first terminal to display an image to be interpreted for an object; an operation reception step of receiving operations performed on the displayed image to be interpreted at the first terminal and the second terminal; an own terminal result display step of causing the first terminal to display a result of processing based on the operation received from the first terminal in real time and causing the second terminal to display a result of processing based on the operation received from the second terminal in real time; a classification step of classifying the operation received from the first terminal into a display operation and a hide operation; and an other terminal result display step of causing the second terminal to display a result of performed display operation in real time in a case where the display operation is performed at the first terminal, and prohibiting the second terminal from displaying a result of performed hide operation in a case where the hide operation is performed at the first terminal. According to the tenth aspect, a plurality of users can efficiently perform the interpretation, similarly to the first aspect. In addition, the interpretation support method according to the tenth aspect may have the same configuration (contents of processing executed by the interpretation support server) as those in the second to eighth aspects.

In order to achieve the above-described object, there is provided an interpretation support program according to an eleventh aspect, the interpretation support program causing an interpretation support server to execute an interpretation support method, in which the interpretation support method includes: an image display step of causing a first terminal connected to the interpretation support server and a second terminal different from the first terminal to display an image to be interpreted for an object; an operation reception step of receiving operations performed on the displayed image to be interpreted at the first terminal and the second terminal; an own terminal result display step of causing the first terminal to display a result of processing based on the operation received from the first terminal in real time and causing the second terminal to display a result of processing based on the operation received from the second terminal in real time; a classification step of classifying the operation received from the first terminal into a display operation and a hide operation; and an other terminal result display step of causing the second terminal to display a result of performed display operation in real time in a case where the display operation is performed at the first terminal, and prohibiting the second terminal from displaying a result of performed hide operation in a case where the hide operation is performed at the first terminal.

According to the eleventh aspect, a plurality of users can efficiently perform the interpretation, similarly to the first aspect. In addition, the interpretation support method executed by the interpretation support program according to the aspect of the present invention may have the same configuration (contents of processing executed by the interpretation support server) as those in the second to eighth aspects. Further, a non-transitory recording medium on which a computer-readable code of the above-described interpretation support program is recorded can also be mentioned as an aspect of the present invention.

In order to achieve the above-described object, there is provided an interpretation terminal according to a twelfth aspect, the interpretation terminal being connected to an interpretation support server, the interpretation terminal comprising a processor, in which the processor is configured to execute: terminal-side image display processing for displaying an image to be interpreted for an object under control of the interpretation support server; terminal-side operation reception processing for receiving an operation of a user on the image to be interpreted; and terminal-side result display processing for displaying a result processed by the interpretation support server according to a classification result in the interpretation support server as to whether the received operation is a display operation that permits display of an operation result on another interpretation terminal connected to the interpretation support server or the received operation is a hide operation that prohibits display of the operation result on the other interpretation terminal, the terminal-side result display processing performing first result display processing for displaying a result of the display operation received by the interpretation terminal and a result of the hide operation received by the interpretation terminal or second result display processing for displaying a result of the display operation received by the other interpretation terminal.

A plurality of interpretation terminals according to the twelfth aspect may be connected to the interpretation support server, and in such a case, a plurality of users can efficiently perform interpretation. Further, the interpretation terminal according to the twelfth aspect may be connected to the interpretation support server according to the first to eighth aspects. In addition, a method executed by the interpretation terminal according to the twelfth aspect (interpretation support method), a program for causing the interpretation terminal to execute the method (interpretation support program), and a non-transitory recording medium in which a computer-readable code of the program is recorded can also be mentioned as aspects of the present invention.

As described above, with the interpretation support server, the interpretation support system, the interpretation support method, the interpretation support program, and the interpretation terminal according to the aspects of the present invention, a plurality of users can access and interpret the same image at the same time, thereby efficiently performing interpretation.

DESCRIPTION OF THE PREFERRED EMBODIMENTS

An embodiment of an interpretation support server, an interpretation support system, an interpretation support method, an interpretation support program, and an interpretation terminal according to the aspects of the present invention will be described. In the description, the accompanying drawings will be referred to as necessary. In the accompanying drawings, some components may be omitted for convenience of description.

First Embodiment

[Configuration of Interpretation Support System]

Figure 1:
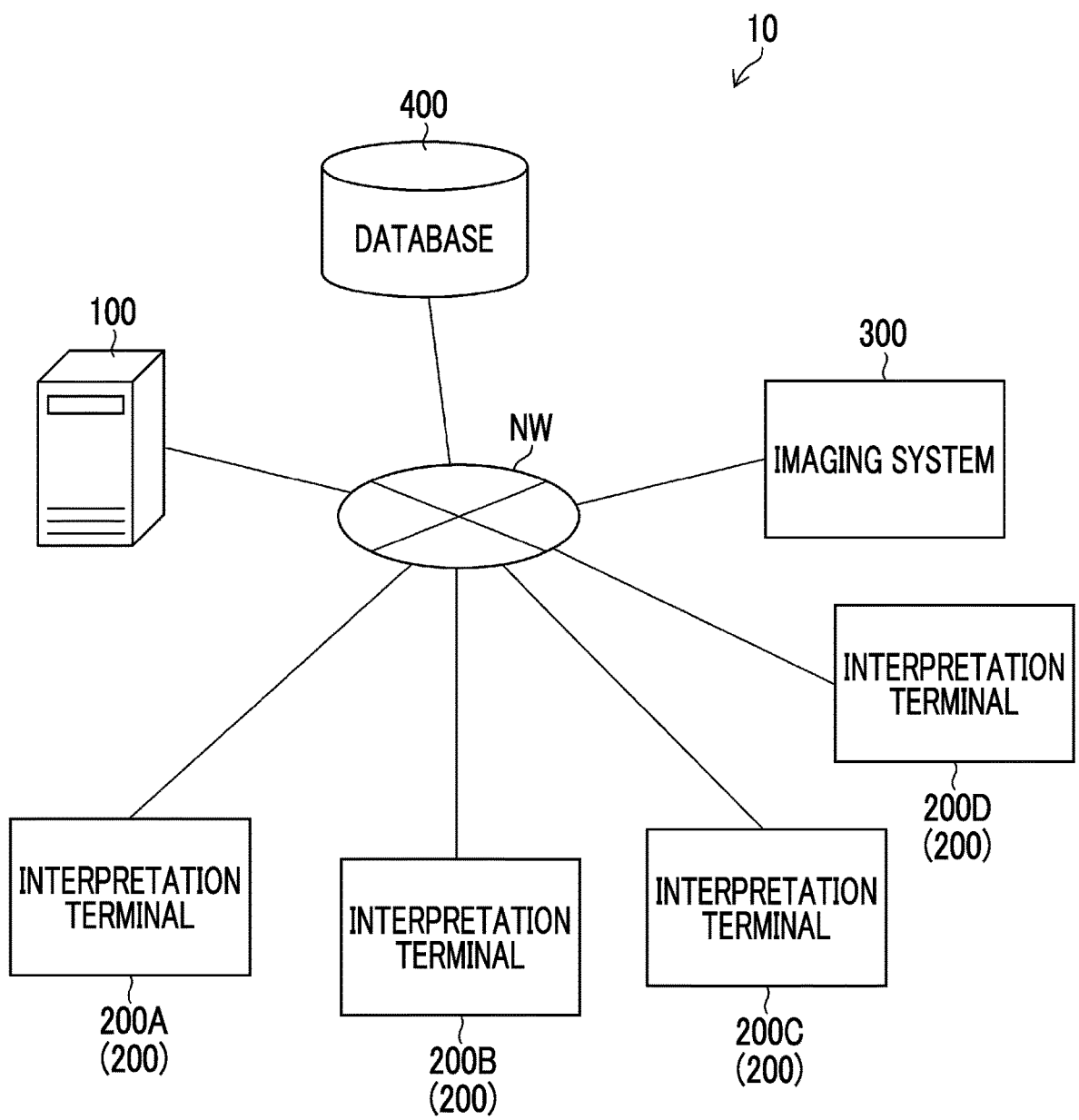
FIG. 1 is a diagram showing a schematic configuration of an interpretation support system according to a first embodiment.

FIG. 1 is a diagram showing a schematic configuration of an interpretation support system 10 (interpretation support system) according to a first embodiment. The interpretation support system 10 is a system that supports a plurality of users to interpret an image (image to be interpreted) of an object on which inspection is to be performed (object). In the first embodiment, a case where the image to be interpreted is a radiation image of an industrial product will be described. However, the interpretation support system according to the first embodiment of the present invention can be applied to other objects and other images to be interpreted as described later. The industrial product, which is an object of interpretation, is not particularly limited to a material such as a metal or a resin, and may be a material before or after the processing, or may be a part or an assembled product.

As shown in FIG. 1, the interpretation support system 10 comprises an interpretation support server 100 (interpretation support server, processor), a plurality of interpretation terminals 200 (first terminal, second terminal, third terminal, fourth terminal), an imaging system 300, and a database 400. In a case where it is necessary to distinguish between a plurality of interpretation terminals 200, the respective interpretation terminals 200 may be referred to as an interpretation terminal 200A, an interpretation terminal 200B, an interpretation terminal 200C, and an interpretation terminal 200D.

The elements described above are connected to each other via a network NW, and communication is performed between the elements as necessary. The connection may be wired or wireless. Further, these components may be stored in a single housing or may be separately stored in a plurality of housings. Although FIG. 1 shows four interpretation terminals 200, the number of interpretation terminals 200 (assuming to be plural) is not limited.

[Configuration of Interpretation Support Server]

Figure 2:
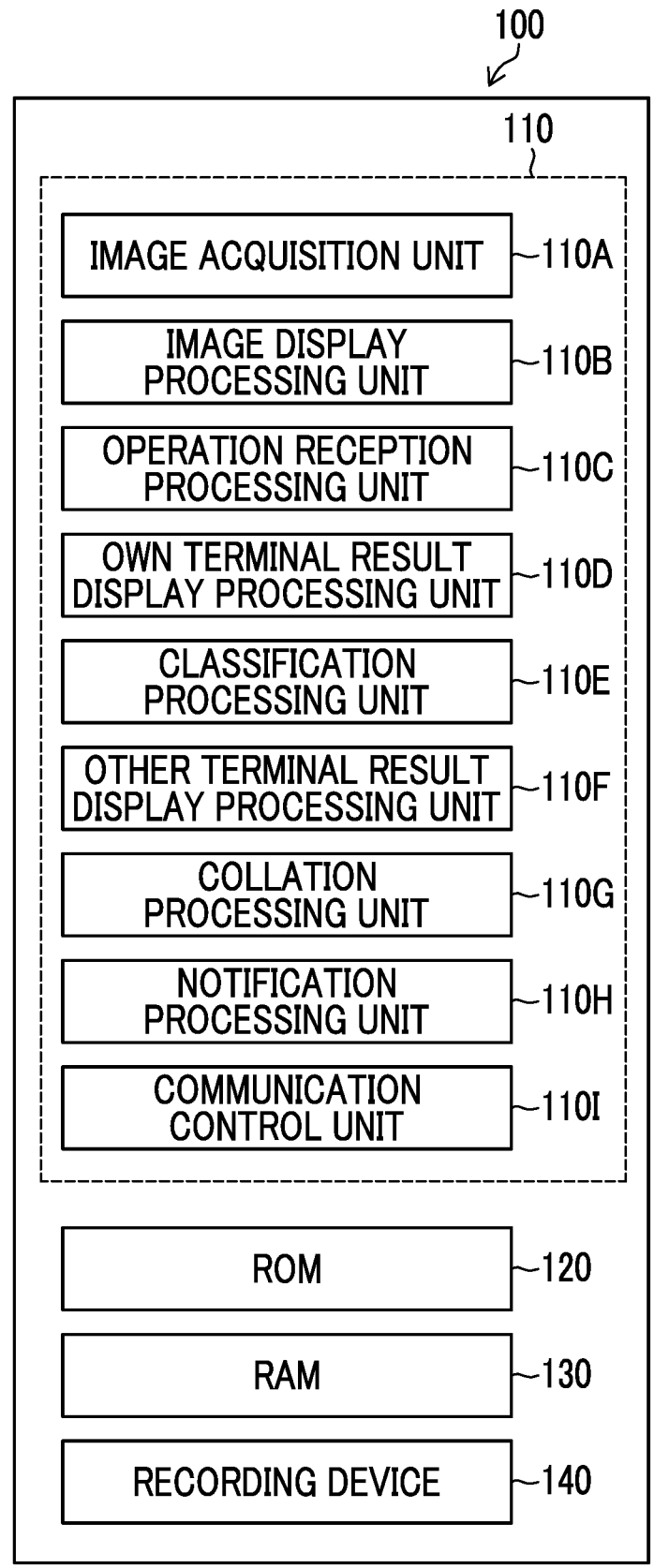
FIG. 2 is a diagram showing a configuration of an interpretation support server.

FIG. 2 is a diagram showing a configuration of the interpretation support server 100. The interpretation support server 100 comprises a processor 110 (processor), a read only memory (ROM) 120, a random access memory (RAM) 130, and a recording device 140. The processor 110 has functions of an image acquisition unit 110A, an image display processing unit 110B, an operation reception processing unit 110C, an own terminal result display processing unit 110D, a classification processing unit 110E, an other terminal result display processing unit 110F, a collation processing unit 110G, a notification processing unit 110H, and a communication control unit 110I.

[Overview of Functions of Processor]

The image acquisition unit 110A acquires an image to be interpreted for an object from the imaging system 300 or the database 400, and the image display processing unit 110B causes a display device of the interpretation terminal 200 to display the image to be interpreted. The operation reception processing unit 110C receives the operation performed by the interpretation terminal 200 as a first terminal for the displayed image to be interpreted. In a case where an operation has been received from the interpretation terminal 200, the own terminal result display processing unit 110D causes the interpretation terminal 200 (own terminal) that has received the operation to display the result of processing based on the received operation in real time. The classification processing unit 110E classifies the received operation into a display operation for causing the interpretation terminal 200 as a second terminal (another terminal) to display the operation result, a first hide operation for causing only some of the interpretation terminals 200 (second terminal) to display the operation result, and a second hide operation for causing only the interpretation terminal 200 (first terminal, own terminal) that has received the operation to display the operation result, and the other terminal result display processing unit 110F causes the interpretation terminal 200 to display the operation result in real time depending on whether the received operation is the display operation or the first or second hide operation.

The collation processing unit 110G performs collation processing of an interpretation range and an interpretation result set in the interpretation terminal 200, and the notification processing unit 110H notifies the user of these collation results. The communication control unit 110I controls communication between the interpretation support server 100 and the interpretation terminal 200 and communication between the interpretation terminals 200.

Details of the processing by each of the above-described units will be described later.

The above-described functions of the processor 110 can be realized by using various processors and a recording medium. The various processors include, for example, a central processing unit (CPU) that is a general-purpose processor that executes software (program) to realize various functions and a programmable logic device (PLD) that is a processor whose circuit configuration can be changed after manufacture, such as a graphics processing unit (GPU), which is a processor specialized in image processing, and a field programmable gate array (FPGA). Each function may be realized by one processor, or may be realized by a plurality of processors of the same type or different types (for example, a plurality of FPGAs, a combination of a CPU and an FPGA, or a combination of a CPU and a GPU). In addition, a plurality of functions may be realized by one processor. The hardware structure of these various processors is, more specifically, an electrical circuit (circuitry) in which circuit elements such as semiconductor elements are combined.

In a case where the processor or the electrical circuit described above executes the software (program), a computer-readable code of software to be executed (for example, various processors and electrical circuits constituting the processor 110, and/or combinations thereof) is stored in a non-transitory recording medium (memory) such as a flash memory or read only memory (ROM) 120, and the computer refers to the software. The program to be executed includes a program (interpretation support program) that executes a method (interpretation support method) according to one aspect of the present invention. In addition, in a case of executing the software, information stored in the recording device 140 (image to be interpreted, interpretation support method, execution condition of interpretation support program, execution result, and the like) is used as necessary. Further, at the time of execution, the random access memory (RAM) 130 is used as the transitory storage area.

[Configuration of Imaging System]

The imaging system 300 is a device that irradiates an object on which inspection is to be performed (object) with X-rays, receives the obtained transmitted radiation, and captures a radiation image (an image to be interpreted). The obtained radiation image is recorded in the recording device 140 and/or the database 400 of the interpretation support server 100.

[Information Stored in Database]

The database 400 includes various types of magneto-optical recording media, semiconductor memories, and a control unit thereof, and records information on an object, an image to be interpreted, an interpretation result, and the like.

[Configuration of Interpretation Terminal]

Figure 3:
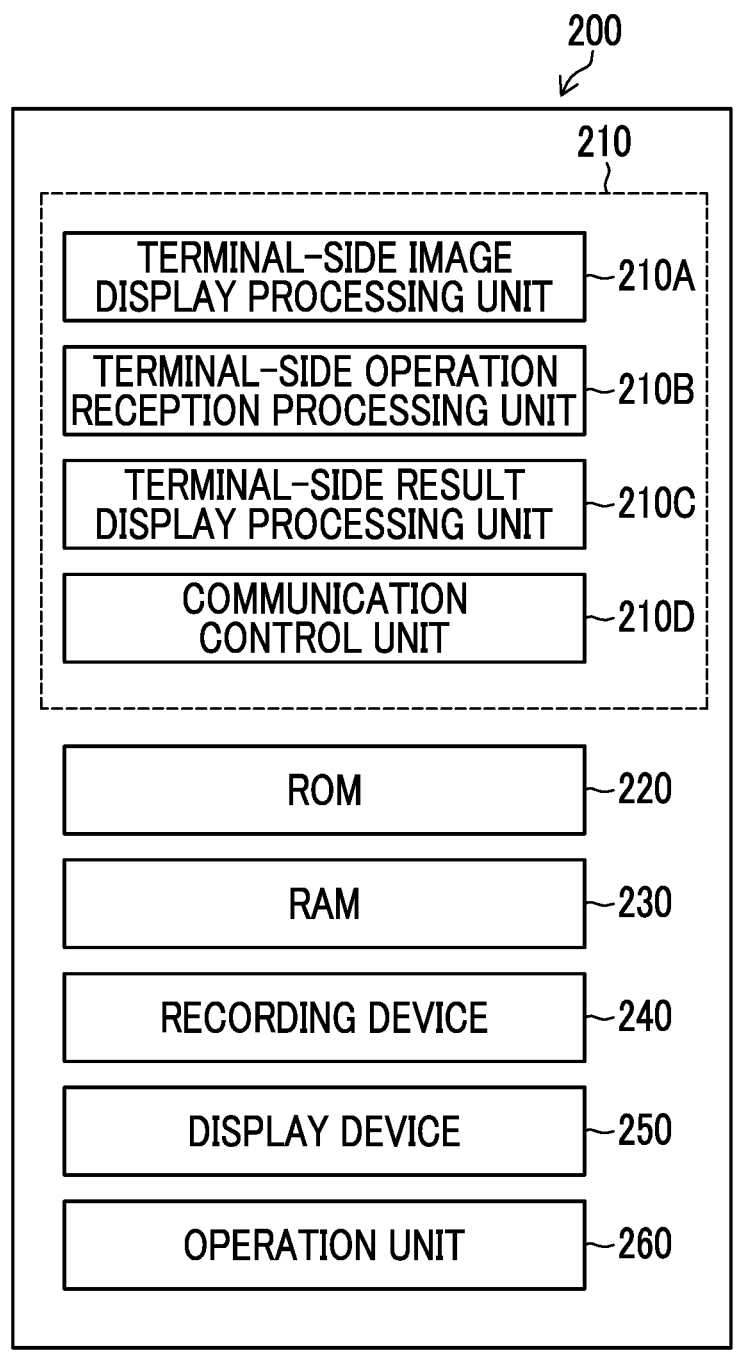
FIG. 3 is a diagram showing a configuration of an interpretation terminal.

FIG. 3 is a diagram showing a configuration of the interpretation terminal 200 (interpretation terminal). The interpretation terminal 200 comprises a processor 210 (processor), a ROM 220, a RAM 230, a recording device 240, a display device 250, and an operation unit 260, and is connected to the interpretation support server 100 via the network NW (see FIG. 1). In the operation of the interpretation terminal 200, the processor 210 refers to the program or data recorded in the ROM 220 and uses the RAM 230 as a transitory processing area. Further, information such as processing conditions, processing results, and operation history is recorded in the recording device 240. The display device 250 is configured by a device such as a liquid crystal display, and can display an image to be interpreted, information indicating an interpretation result, information for performing the interpretation, a result of a display operation, and results of first and second hide operations under the control of the interpretation support server 100. The user can input the above-described information via the operation unit 260 such as a keyboard or a mouse. The display device 250 may be configured by a touch panel type monitor, and the user may give an instruction via the touch panel.

The processor 210 includes a terminal-side image display processing unit 210A, a terminal-side operation reception processing unit 210B, a terminal-side result display processing unit 210C, and a communication control unit 210D. These functions can be realized for the processor 110 of the interpretation support server 100 using various processors and a recording medium in the same manner as described above.

The interpretation terminal 200 having the above-described configuration operates as a first terminal and a second terminal in the present invention.

[Processing in Interpretation Support System]

[Display of Image to be Interpreted]

Figure 4:
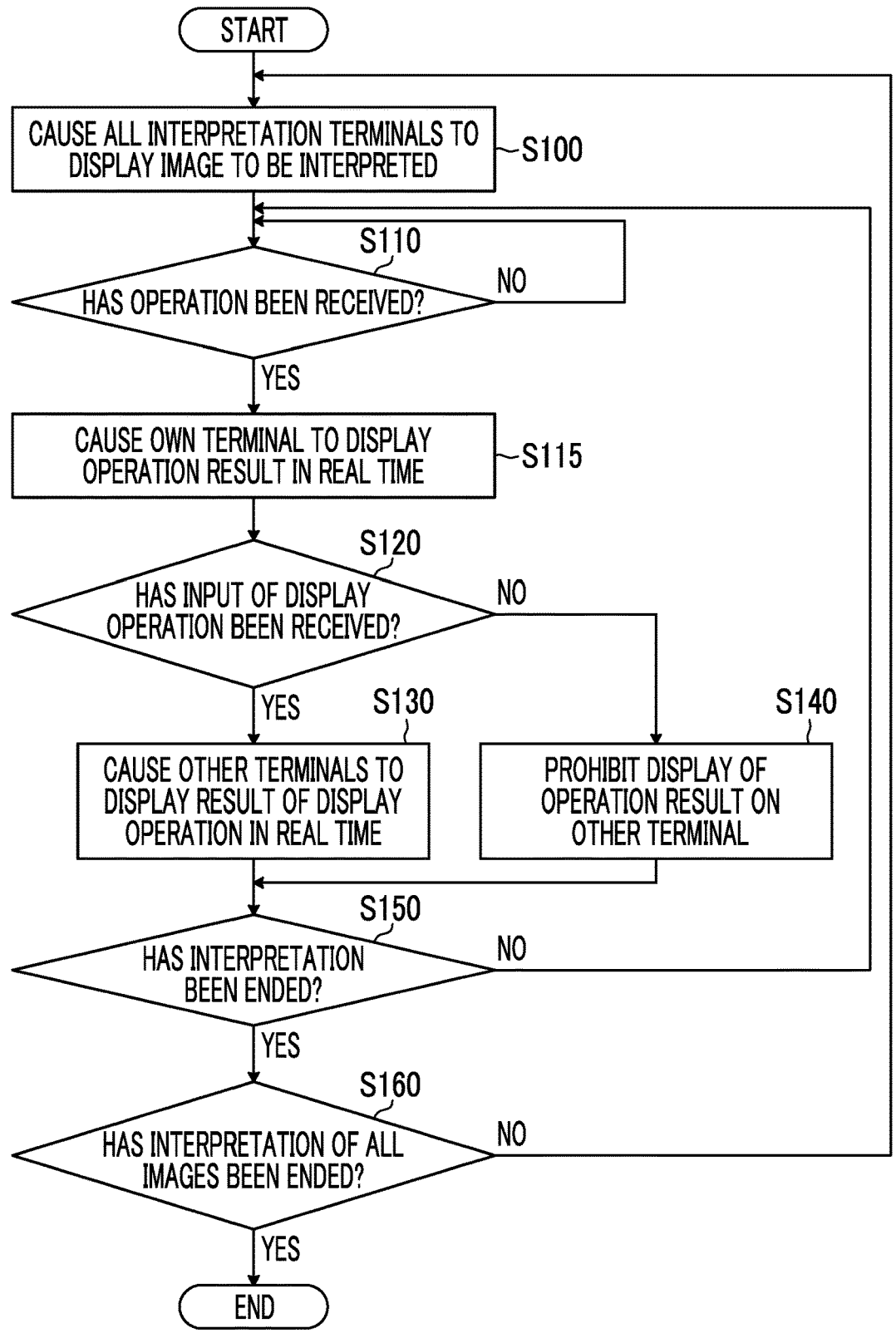
FIG. 4 is a flowchart showing processing in the interpretation support server.

The processing in the interpretation support system 10 will be described. FIG. 4 is a flowchart showing processing in the interpretation support server 100. The processor 110 (image acquisition unit 110A, image display processing unit 110B) of the interpretation support server 100 causes a plurality of interpretation terminals 200 (display devices 250) connected to the interpretation support server 100 to display an image to be interpreted for an object (Step S100: image display step, image display processing). The processor 210 (terminal-side image display processing unit 210A) of the interpretation terminal 200 causes the display device 250 to display the image to be interpreted in response to the control of the interpretation support server 100. The image to be interpreted may be an image directly acquired by the interpretation support server 100 from the imaging system 300, an image recorded in the database 400, or an image recorded in the recording device 140 of the interpretation support server 100. In addition, the interpretation support server 100 may sequentially display images stored in a predetermined folder as images to be interpreted, or may display images designated by the user via the interpretation terminal 200. The image to be interpreted is displayed on the interpretation terminal 200 under the control of the processor 110 (see FIGS. 5A to 11; terminal-side image display processing, terminal-side image display step).

In addition, the interpretation support server 100 can recognize the interpretation terminal that has received the operation of the user among the plurality of interpretation terminals 200 as the "first terminal", and recognize the other interpretation terminals (interpretation terminals different from the first terminal) as the "second terminals". Since any of the interpretation terminals 200 can receive the operation of the user, the recognition of the first terminal and the second terminal is not fixed, and even in a case where a specific interpretation terminal 200 (for example, the interpretation terminal 200A) is recognized as the first terminal for a certain operation, another interpretation terminal 200 (for example, the interpretation terminal 200B) may be recognized as the first terminal for another operation. Further, in a case where the plurality of interpretation terminals 200 receive the operation at close timings, any one of the interpretation terminals 200 can be recognized as the first terminal, and the other interpretation terminals 200 can be recognized as the second terminals.

[Reception of Operations and Display of Results on Own Terminal]

In a case where the user operates the interpretation terminal 200 via the operation unit 260, the processor 210 (terminal-side operation reception processing unit 210B) receives the processing, and in response to this, the processor 110 (operation reception processing unit 110C) of the interpretation support server 100 determines whether or not an operation performed at the interpretation terminal 200 (the first terminal and the second terminal) has been received for the displayed image to be interpreted (Step S110: operation reception processing, operation reception step). In a case where the operation has been received (YES in Step S110), the processor 110 (own terminal result display processing unit 110D) performs processing based on the operation received from the interpretation terminal 200, and causes the first terminal that has received the operation to display a result of the processing in real time (Step S115: own terminal result display processing, own terminal result display step). For example, the processor 110 performs processing based on an operation received from the interpretation terminal 200A, and causes the interpretation terminal 200A to display a result of the processing in real time (for example, displays the result on an individual display screen to be described later). Similarly, the processor 110 performs processing based on an operation received from the interpretation terminal 200B, and causes the interpretation terminal 200B to display a result of the processing in real time. The same applies to a case where the interpretation terminal 200C receives an operation.

The processor 110 (own terminal result display processing unit 110D) causes the first terminal at which the display operation is performed to display the result of the display operation performed at the first terminal in real time. For example, in a case where the interpretation terminal 200A (own terminal, first terminal) receives the display operation, the processor 110 causes the interpretation terminal 200A itself (own terminal, first terminal) to display the result of the display operation (Step S115: own terminal result display processing, own terminal result display step). The processor 210 (terminal-side result display processing unit 210C) causes the display device 250 (own terminal, first terminal) to display the result of the display operation under the control of the processor 110 (terminal-side result display processing, terminal-side result display step, first result display processing, first result display step). The processor 210 can display, for example, the result of the display operation on the own terminal on the entire display screen (see FIGS. 5A to 11).

[Classification of Operations]

In a case where the interpretation terminal 200 receives the operation (YES in Step S110), the processor 110 (classification processing unit 110E) determines whether or not the input of the display operation has been received (Step S120: classification processing, classification step). Specifically, the processor 110 (classification processing unit 110E) classifies the operation received from the interpretation terminal 200 (first terminal) into a display operation that permits display of the operation result on another interpretation terminal 200 (second terminal) and a hide operation that prohibits display of the operation result on another interpretation terminal 200 (Step S120: classification processing, classification step). For example, the processor 110 classifies the operation received from the interpretation terminal 200A (first terminal) (terminal-side operation reception processing operation received in the terminal-side operation reception step) into a display operation that permits display of the operation results on the interpretation terminals 200B and 200C (other second terminals) and a hide operation that prohibits display of the operation results on the interpretation terminals 200B and 200C (other second terminals). In addition, for example, in a case where the operation has been received from the interpretation terminal 200B (first terminal), the processor 110 classifies the operation into a display operation that permits display of the operation results on the interpretation terminals 200A and 200C (other second terminals) and a hide operation that prohibits display of the operation results on the interpretation terminals 200A and 200C (other second terminals).

In Step S120 (classification processing, classification step), the processor 110 (classification processing unit 110E) can classify, as a display operation, an operation in which users of the first terminal and the second terminal input information indicating an interpretation result of the image to be interpreted, and classify, as a hide operation, an operation in which the user of the first terminal inputs information regarding processing of the image to be interpreted.

Specifically, the processor 110 can receive, as "information indicating the interpretation result", at least one of the number, position, type, degree, or reason for determining the degree of defects in the image to be interpreted to classify an operation of inputting the information into a "display operation", and receive, as "information regarding processing of the image to be interpreted", at least one of an enlarging or reducing operation, a moving operation, a rotating operation, a transforming operation, an operation of changing a gradation, an operation of setting an interpretation range, an operation of designating a defect, or an operation of setting interpretation content for the image to be interpreted to classify an operation of inputting the information into a "hide operation".

[Display of Operation Result (in Case of Display Operation)]

In a case where it is determined in Step S120 that "the received operation is a display operation" (the determination result is YES), the processor 110 (other terminal result display processing unit 110F) of the interpretation support server 100 causes the second terminal (another terminal) to display the result of the display operation performed at the first terminal (own terminal) in real time. For example, in a case where the interpretation terminal 200A (own terminal, first terminal) receives the display operation, the processor 110 causes the interpretation terminals 200B and 200C (other terminals, second terminals) to display the result of the display operation (Step S130: other terminal result display processing, other terminal result display step, first result display processing, first result display step). The processor 210 (terminal-side result display processing unit 210C) of the interpretation terminal 200 causes the display device 250 to display the result of the display operation according to the control of the processor 110 according to the classification result of the operation (terminal-side result display processing, terminal-side result display step, second result display processing, second result display step). The processor 210 can display the result of the display operation on the entire display screen of the display device 250 (another terminal) (see FIGS. 5A to 11 to be described later).

[Display of Operation Result (in Case of Hide Operation)]

In a case where it is determined in Step S120 that "the received operation is a hide operation" (the determination result is NO), the processor 110 (own terminal result display processing unit 110D) of the interpretation support server 100 prohibits the second terminal from displaying the result of the hide operation performed at the first terminal (Step S140: own terminal result display processing, own terminal result display step). For example, in a case where the interpretation terminal 200A (first terminal) receives the hide operation, the processor 110 prohibits the interpretation terminals 200B and 200C (second terminals) from displaying the result of the hide operation. Similarly, in a case where the interpretation terminal 200B (first terminal) receives the hide operation, the processor 110 prohibits the interpretation terminals 200A and 200C (second terminals)

from displaying the result of the hide operation. The same applies to a case where the interpretation terminal 200C (first terminal) receives a hide operation.

The processor 210 (terminal-side result display processing unit 210C) of the interpretation terminal 200 causes the display device 250 to display the result of the hide operation according to the control of the processor 110 according to the classification result of the operation (terminal-side result display processing, terminal-side result display step, first result display processing, first result display step). The processor 210 can display the result of the hide operation on the individual display screen (see FIGS. 5A to 11 to be described later).

[End of Processing]

After the display of the operation result is ended, the processor 110 determines whether or not the interpretation has been ended (Step S150) and whether or not the interpretation of all the images to be interpreted has been ended (Step S160). The processor 110 may determine "whether or not the interpretation has been ended" based on an operation (for example, a click of the "interpretation end" button) with the "interpretation end" in the interpretation terminal 200, or the interpretation support server 100 may determine that "interpretation has been ended" (for example, in a case where the interpretation progress status is in the state shown in FIGS. 9A and 9B). In addition, in a case where the interpretation of all images stored in a predetermined folder or all designated images (for example, flagged as interpretation targets) has been ended, the processor 110 can determine that "interpretation of all images to be interpreted has been ended".

[Example of Screen Display on Interpretation Terminal]
[Setting of Interpretation Range and Omission Check]

Figure 5A:
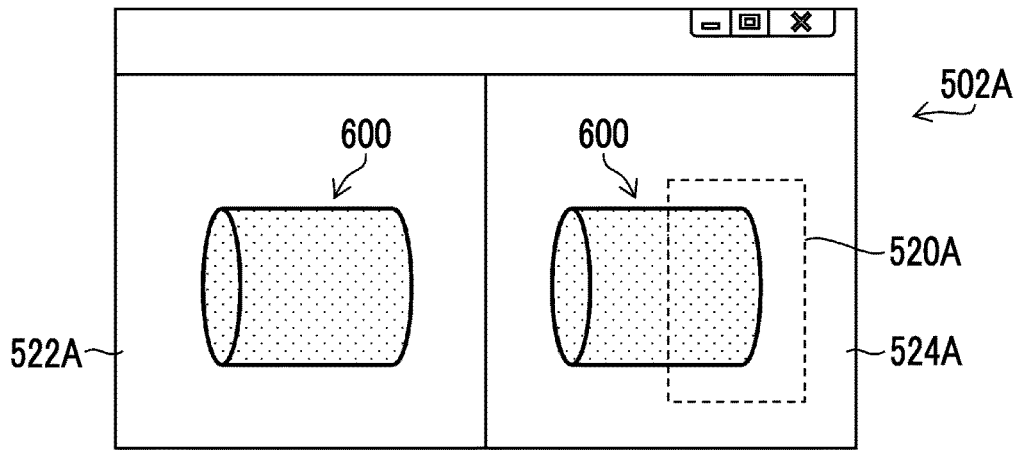
FIGS. 5A to 5C are diagrams showing a state in which an interpretation range is set and an omission check is performed.
Figure 5B:
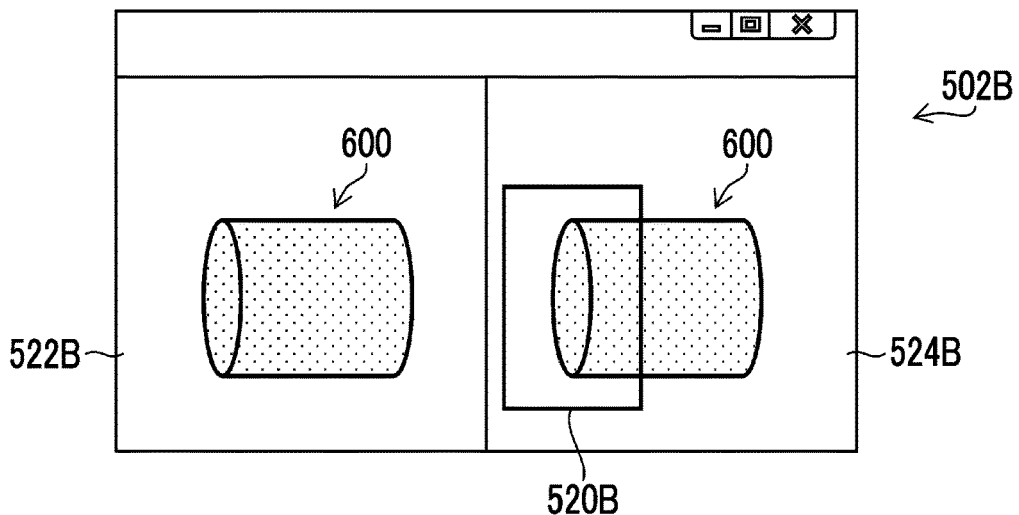
Figure 5C:
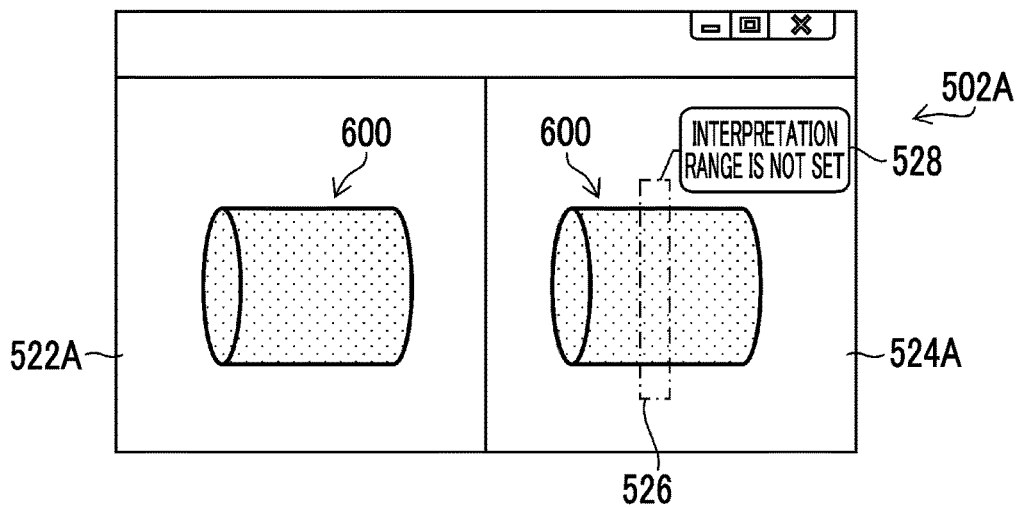

Next, a specific example of screen display on the interpretation terminal will be described. FIGS. 5A to 5C are diagrams showing a state in which an interpretation range is set and an omission check is performed. FIG. 5A shows a screen 502A of the display device 250 of the interpretation terminal 200A (assuming that the user is engineer A). The screen 502A includes an entire display screen 522A and an individual display screen 524A, and the example of FIG. 5A shows a state in which the image of a cylindrical object 600 (image to be interpreted) is displayed (results of image display processing, terminal-side image display processing, etc.). The entire display screen 522A is a screen on which the result of the display operation on the own terminal and other terminals is displayed, and the individual display screen 524A is a screen on which the result of the hide operation by the user of the interpretation terminal 200A is displayed.

Similarly, FIG. 5B shows a screen 502B of the display device 250 of the interpretation terminal 200B (assuming that the user is engineer B). The screen 502B includes an entire display screen 522B and an individual display screen 524B.

In the situation described above, it is assumed that the operation of setting an interpretation range 520A is performed by the interpretation terminal 200A and the operation of setting an interpretation range 520B is performed by the interpretation terminal 200B. Then, the processor 110 receives the operation of setting the interpretation ranges 520A and 520B on the image to be interpreted as "information regarding processing of the image to be interpreted" (operation reception processing, operation reception step) and classifies the operation as a "hide operation" (classification processing, classification step). The processor 110 (collation processing unit 110G, notification processing unit 110H) confirms whether or not a region in which the object 600 is shown in the image to be interpreted is entirely covered by the set interpretation ranges 520A and 520B (collation processing, collation step), and notifies the user of the interpretation terminal 200 of the confirmation result (notification processing, notification step). The interpretation terminal 200 (the terminal-side result display processing unit 210C) provides the notification by the display device 250 under the control of the processor 110. A speaker (not shown) may be used for notification by voice.

FIG. 5C is a diagram showing an example of notification (the screen of the interpretation terminal 200A) (the similar notification method can be used for another interpretation terminal 200). In this example, an interpretation range is not set for a region 526 in any of the interpretation terminals. Therefore, the processor 110 identifies and displays the region 526 with a frame line, and displays a message 528 indicating that the interpretation range is not set. With such notification, the user can easily recognize the omission of the interpretation range, and it is possible to prevent the omission from occurring.

[Display Example of Result of Hide Operation]

Figure 6A:
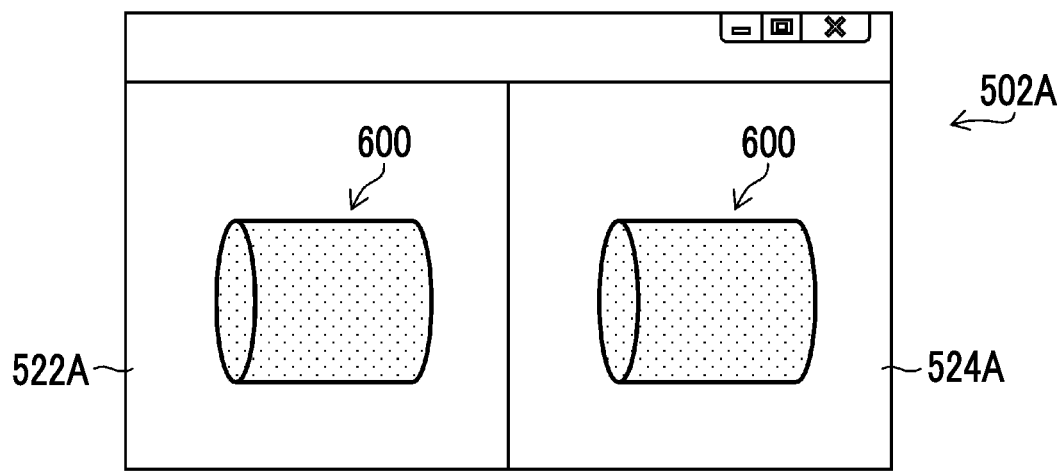
FIGS. 6A and 6B are diagrams showing an example of a hide operation on an image to be interpreted.
Figure 6B:
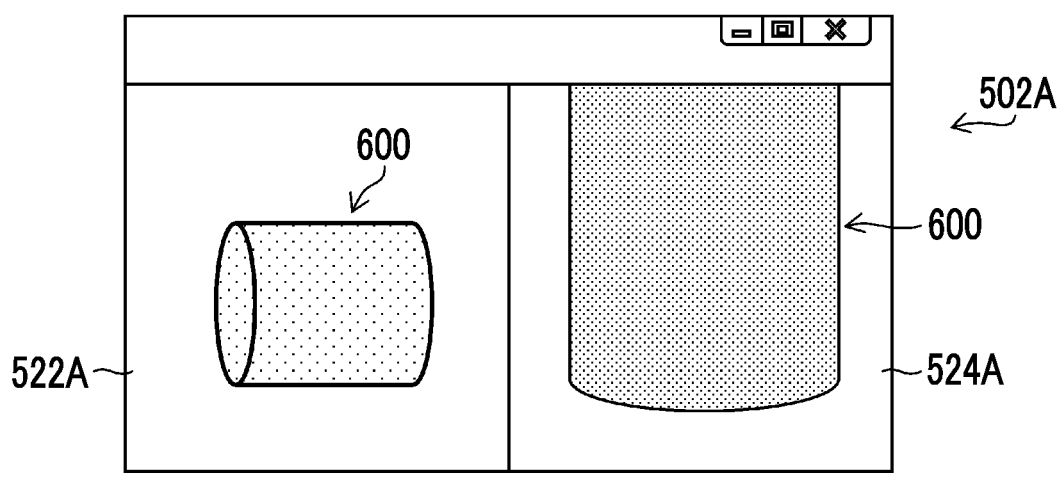

FIGS. 6A and 6B are diagrams showing a display example of the result of the hide operation. FIG. 6A shows a state (a state before the operation) in which the object 600 is displayed on the entire display screen 522A and the individual display screen 524A as in FIGS. 5A to 5C. In a case where the image is rotated and the brightness is changed (an example of the hide operation) on the individual display screen 524A in this state, the processor 110 classifies these operations as hide operations, causes only the interpretation terminal 200A (own terminal) to display the operation results on the interpretation terminal 200A (own terminal) (state shown in FIG. 6B), and does not cause the interpretation terminals 200B and 200C (other terminals) to display the operation results (Step S140: own terminal result display processing, own terminal result display step). In addition, in a case where the interpretation terminal 200B receives the rotation of the image and the change in the brightness, the processor 110 does not cause the interpretation terminals 200A and 200C to display the result, and in a case where the interpretation terminal 200C receives these operations, the processor 110 does not cause the interpretation terminals 200A and 200B to display the result. In this way, in the interpretation support system 10, operations with different conditions depending on the user and operations that do not require sharing of results are not displayed on the entire display screen, but displayed only on the individual display screen. Therefore, a plurality of users can efficiently perform interpretation under desired conditions.

[Display Example of Result of Display Operation (Input of Interpretation Result)]

Figure 7A:
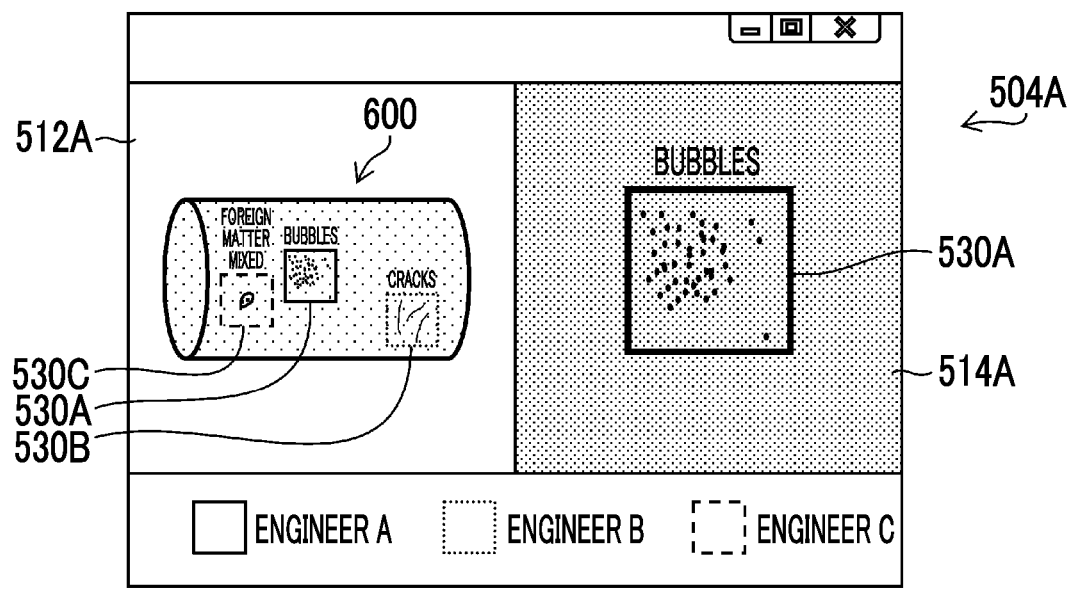
FIGS. 7A and 7B are diagrams showing a state in which an interpretation result is input and the result is displayed on an entire display screen.
Figure 7B:
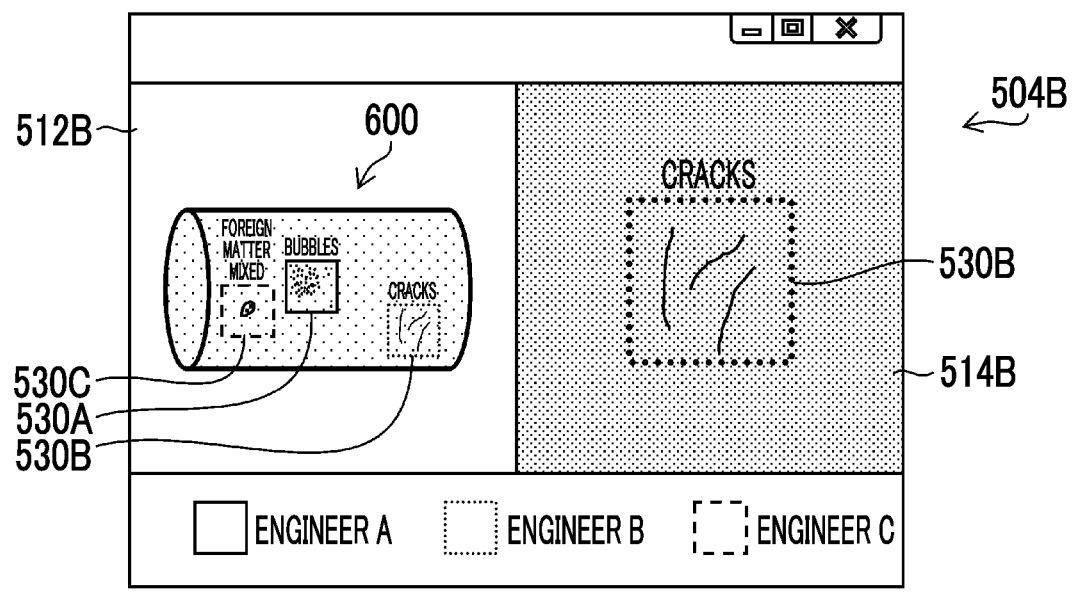

FIGS. 7A and 7B are diagrams showing a display example of the result of the display operation. FIG. 7A shows a screen 504A (entire display region 512A, individual display region 514A) of the interpretation terminal 200A, and FIG. 7B shows a screen 504B (entire display region 512B, individual display region 514B) of the interpretation terminal 200B. An image of the object 600 (image to be interpreted) and an interpretation result thereof are displayed in the entire display regions 512A and 512B, and an image of the object 600 (image to be interpreted) is displayed in the individual display regions 514A and 514B. The users of the interpretation terminals 200A and 200B interpret the image to be interpreted by being enlarged as necessary in the individual display regions 514A and 514B, and input the results. In the example shown in FIGS. 7A and 7B, the user of the interpretation terminal 200A inputs that there are bubbles (an example of a defect) in a region 530A in the individual display region 514A, and the user of the interpretation terminal 200B inputs that there are cracks (an example of a defect) in a region 530B in the individual display region 514B. In addition to this, it is assumed that in the interpretation terminal 200C, it is input that the foreign matter is mixed in a region 530C.

In this case, the processor 110 receives an input operation in each interpretation terminal and classifies the input operation as an "operation for inputting an interpretation result", that is, a "display operation". Then, the processor 110 causes the interpretation terminals 200A (own terminal, first terminal) and the interpretation terminals 200B and 200C (other terminals, second terminals) to display the result of the operation in the interpretation terminal 200A in real time, causes the interpretation terminal 200B (own terminal, first terminal) and the interpretation terminals 200A and 200C (other terminals, second terminals) to display the result of the operation in the interpretation terminal 200B (own terminal, first terminal) in real time, and causes the interpretation terminal 200C (own terminal, first terminal) and the interpretation terminals 200A and 200B (other terminals, second terminals) to display the result of the operation in the interpretation terminal 200C (own terminal, first terminal) in real time. The processor 210 displays the interpretation result in the entire display regions 512A and 512B under the control of the interpretation support server 100 (similarly, the interpretation terminal 200C also displays the interpretation result, but it is not shown in FIGS. 7A and 7B).

The processor 110 identifies and displays the interpretation result of the region 530A in association with the fact that the interpretation result is input from the interpretation terminal 200A, and identifies and displays the interpretation result of the region 530B in association with the fact that the interpretation result is input from the interpretation terminal 200B. Specifically, the processor 110 identifies and displays the interpretation result in each interpretation terminal by indicating frame lines of the regions 530A and 530B with different line types. The processor 110 can perform association and identification display using characters, numbers, symbols, figures, or a combination thereof, and the color or brightness of the display may be changed for each interpretation terminal. In addition, as shown in FIGS. 7A and 7B, the processor 110 can cause the interpretation terminal to display a user's name, ID, or the like such as "engineer A", "engineer B", or "engineer C" in association with the interpretation result (the same applies to other figures). Although FIGS. 7A and 7B show that the interpretation results are different for different users due to the difference in line types indicating the region, the color of the line type may be changed depending on the user.

By displaying the interpretation result in this way, each user can easily grasp which user performed what interpretation, and thereby the likelihood of erroneous interpretation can be reduced.

[Display Example of Interpretation Progress Status]

Figure 8A:
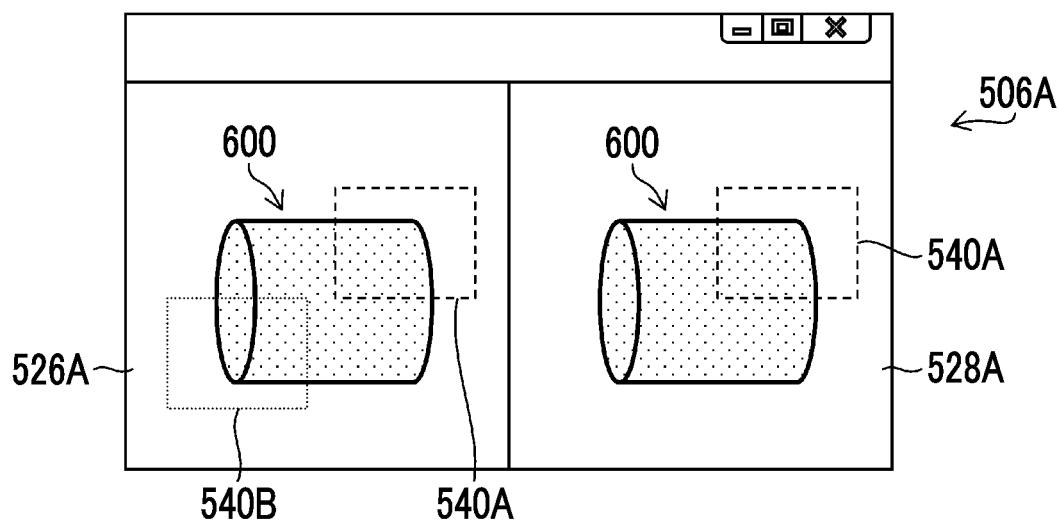
FIGS. 8A and 8B are diagrams showing a display example of an interpretation progress status.
Figure 8B:
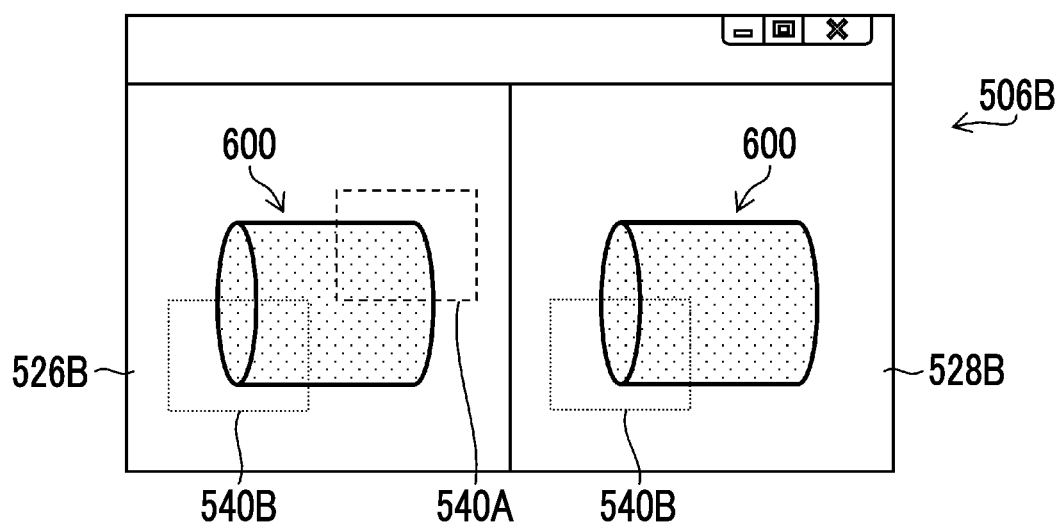
Figure 9A:
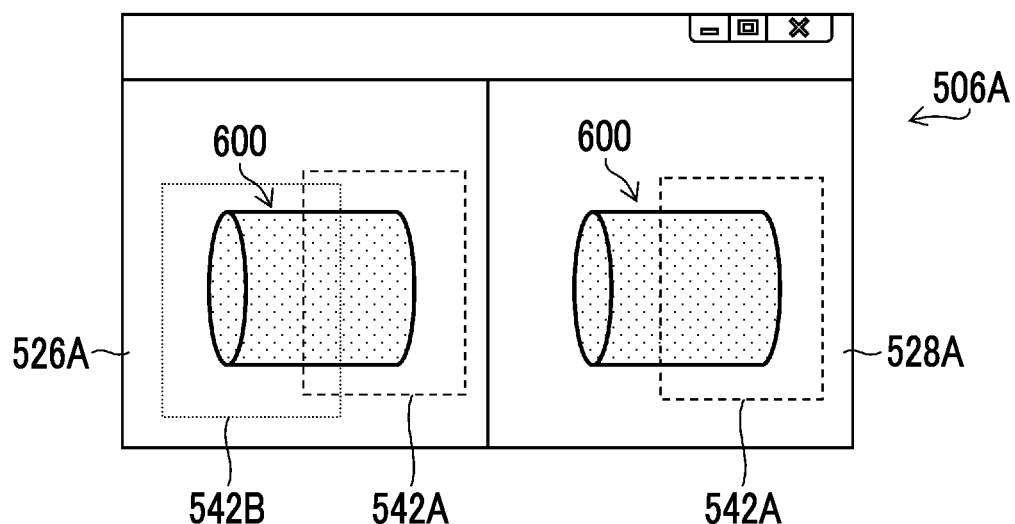
FIGS. 9A and 9B are other diagrams showing a display example of an interpretation progress status.
Figure 9B:
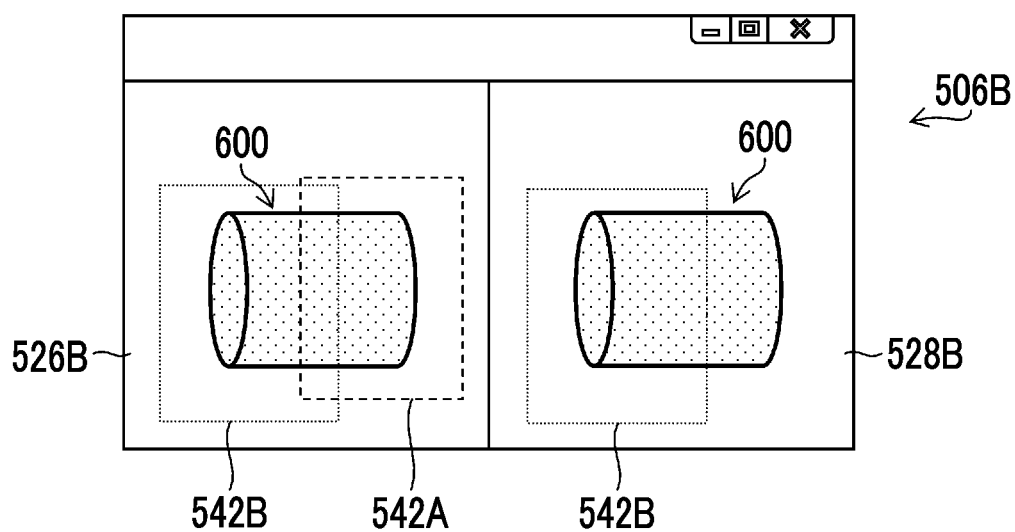

FIGS. 8A to 9B are diagrams showing a display example of the interpretation progress status (in a case where the interpretation is performed by the interpretation terminals 200A and 200B). FIGS. 8A and 8B show a state during interpretation, and FIGS. 9A and 9B show a state in which interpretation is completed for the entire range of a certain image to be interpreted.

FIG. 8A shows a screen (entire display region 526A, individual display region 528A; display device 250) of the interpretation terminal 200A, and FIG. 8B shows a screen (entire display region 526B, individual display region 528B; display device 250) of the interpretation terminal 200B. In a case where the interpretation is performed for regions 540A and 540B in the individual display regions 528A and 528B of the interpretation terminals 200A and 200B, respectively, the processor 110 and the processor 210 display the results in real time in the entire display regions 526A and 526B. In addition, as shown in FIGS. 9A and 9B, after the interpretation is ended for regions 542A and 542B in the interpretation terminals 200A and 200B, respectively, the processor 110 and the processor 210 display the results in real time in the entire display regions 526A and 526B.

In a case where the interpretation progress status is displayed, the processor 110 can handle the interpretation progress status as "information indicating the interpretation result", that is, a "display operation". In addition, the processor 110 can determine the progress or end of the interpretation based on the operations of the interpretation terminals 200A and 200B (for example, clicking of a button indicating that the interpretation has been ended for the designated region).

With such a display, the user can easily grasp an interpretation progress status and can prevent the interpretation from being omitted (FIGS. 9A and 9B show an example in which there is no omission in the interpretation range).

[Other Display Examples of Image to be Interpreted]

Figure 10:
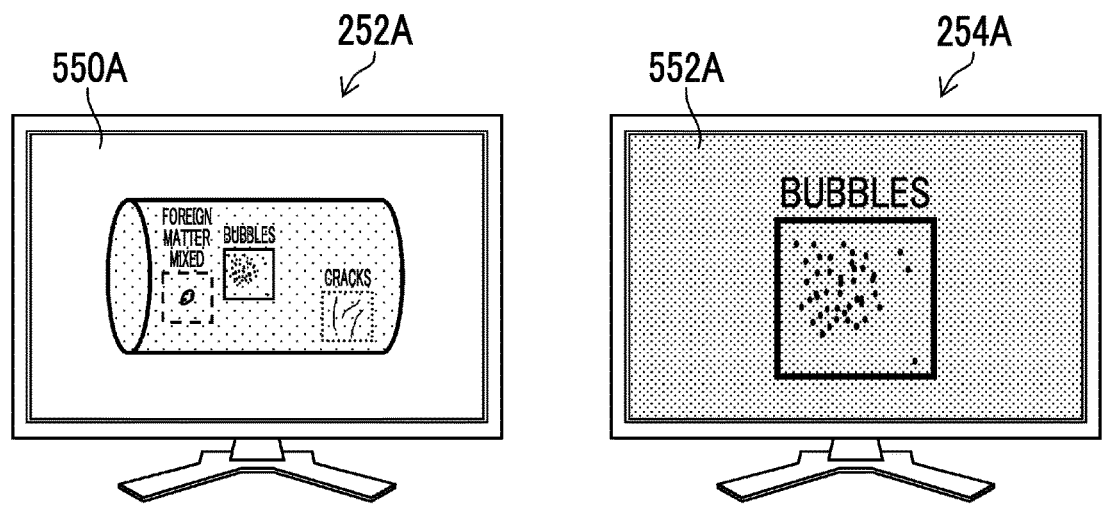
FIG. 10 is a diagram showing a state in which screens are displayed on each of a plurality of monitors.

FIGS. 5A to 9B described above show an example in which the entire display region and the individual display region are displayed on one screen (window). However, in the interpretation support system 10, the entire display region and the individual display region may be displayed on different screens (windows). In addition, as shown in FIG. 10, two display devices 252A and 254A may display an entire display region 550A and an individual display region 552A, respectively.

Figure 11:
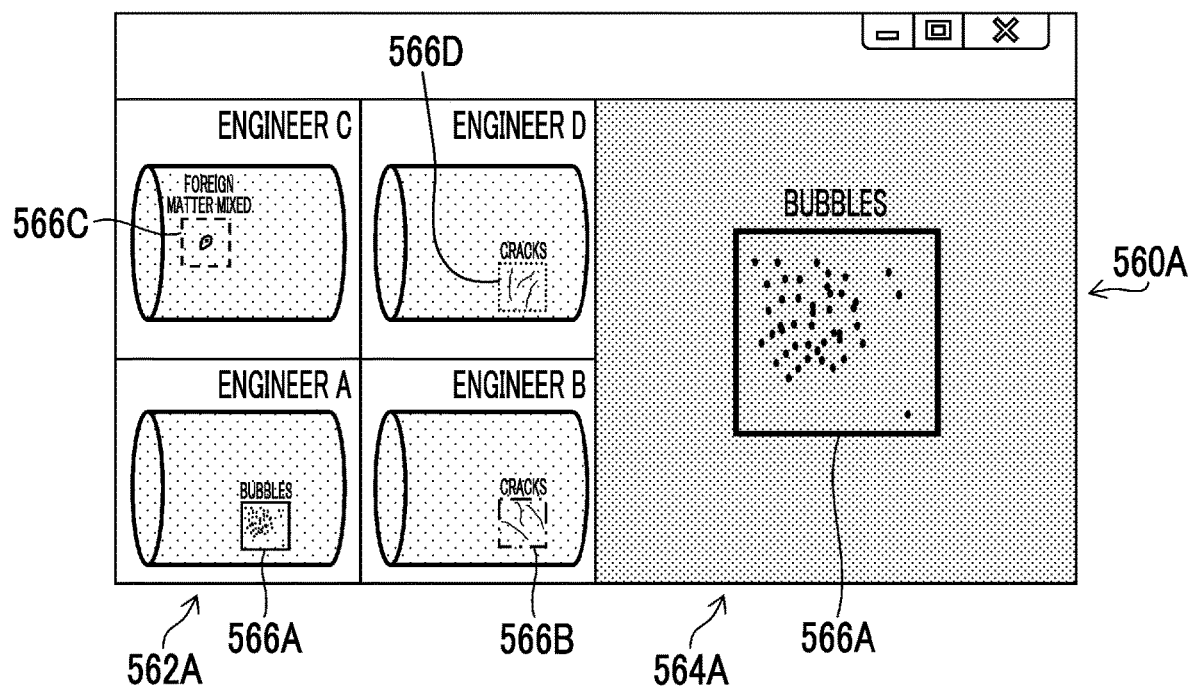
FIG. 11 is a diagram showing a state of interpretation of a plurality of objects.

In addition, in the interpretation support system 10, a plurality of images to be interpreted may be displayed on the interpretation terminal 200, or an image in which a plurality of objects are shown may be displayed. FIG. 11 is an example showing a state in which images of a plurality of objects are displayed on a screen 560A (an entire display region 562A and an individual display region 564A) of the interpretation terminal 200A. The example of FIG. 11 shows a state in which four images of the object 600 are displayed in an entire display region 562A, and four users (engineer A to engineer D) are in charge of interpreting one object 600, respectively. Each user inputs interpretation results (position and type of defect) in regions 566A to 566D, respectively. For example, in a case where engineer A who is a user of the interpretation terminal 200A inputs the region 566A as the "region where bubbles exist" in the individual display region 564A, the processor 110 classifies the operation as a "display operation" and causes all interpretation terminals to display the processing results in real time. Accordingly, each user can easily recognize the result of the display operation by other users, and a plurality of users can efficiently perform the interpretation in the same manner as in the above-described aspect.

Note that, in a case where images of a plurality of objects are displayed, the objects may be of the same type or different types.

Effect of First Embodiment

As described above, in the interpretation support system 10 according to the first embodiment, the interpretation support server 100 (processor 110) classifies the operations received by the interpretation terminal 200 into a display operation and a hide operation (first display operation, second display operation), and causes the own terminal and other terminals to display results according to the classification results. Operation results (results of display operations) that should be confirmed by all users, such as input of interpretation results, can be displayed in real time on the entire display screen, and individual operation results (results of the first display operation and results of the second display operation), such as enlargement or reduction of an image can be displayed in real time on the individual display screen. Therefore, it is possible to reduce the likelihood of omission or error in the interpretation, and the user can perform the interpretation under desired conditions without being bothered by unnecessary display. Thus, according to the first embodiment, a plurality of users can simultaneously access the same image and perform interpretation efficiently.

Modification Example: Sharing Result of Hide Operation

Figure 12:
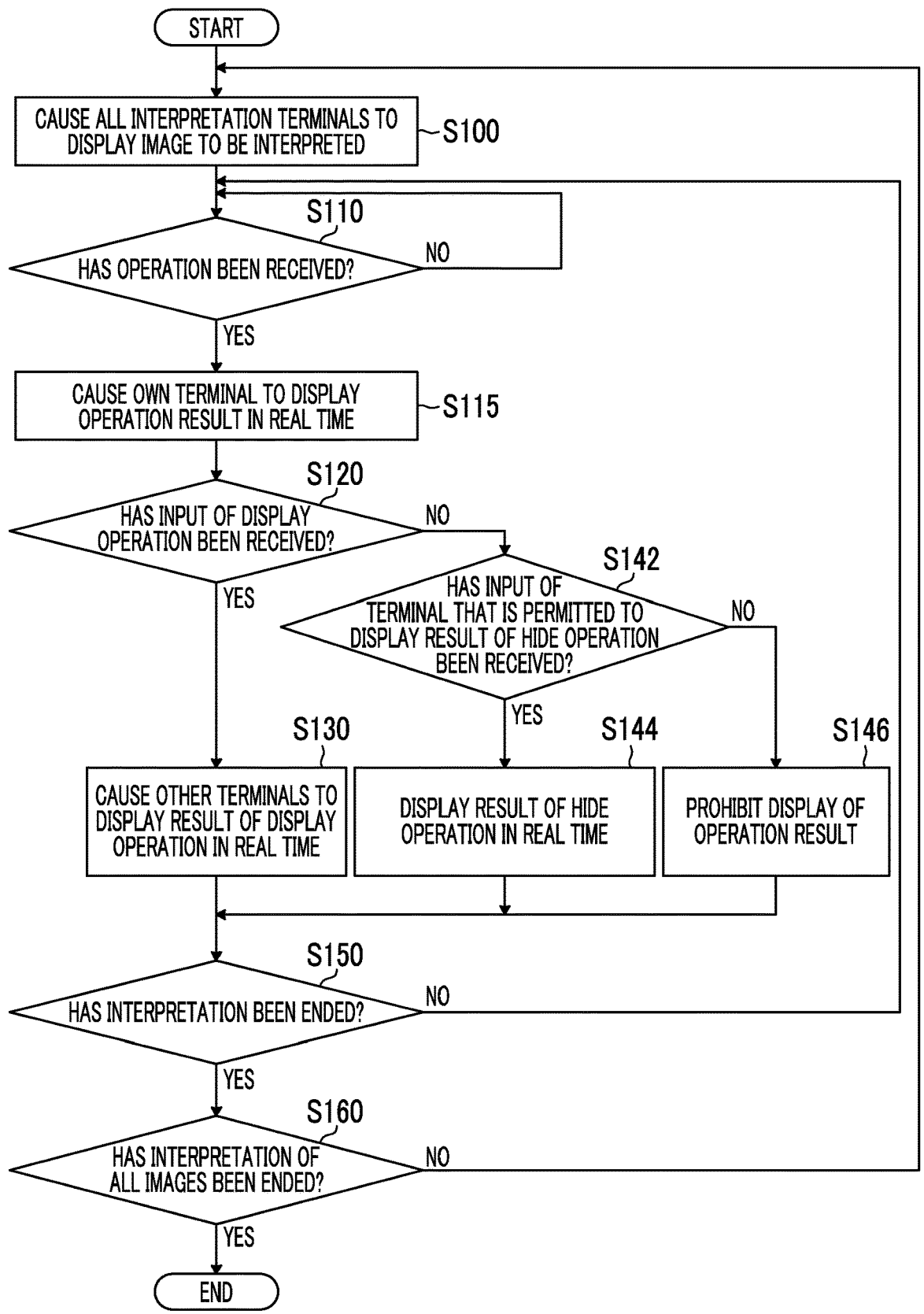
FIG. 12 is another flowchart showing processing in the interpretation support server.

In the interpretation, a process in a case where a user desires to share the result of a hide operation with some users will be described. FIG. 12 is a flowchart showing processing in such a case.

For example, it is assumed that a user (engineer A) of the interpretation terminal 200A desires to share the result of the hide operation only with a user (engineer B) of the interpretation terminal 200B, and the user (engineer B) of the interpretation terminal 200B agrees to this (conversely, also in a case where engineer B desires to share the operation results with engineer A, the same process can be performed). For example, it is conceivable that engineer A wants to consult or ask a question about the items entered by engineer B, or that engineer A and engineer B desire to perform interpretation under common screen display conditions (enlargement/reduction, rotation, movement, change in brightness, etc. of images). In this case, engineer A operates the interpretation terminal 200A and performs an operation of designating that the operation result is to be shared with the interpretation terminal 200B. The terminal-side operation reception processing unit 210B (processor 210) of the interpretation terminal 200A receives a user's operation (including operation content and designation of a sharing partner user or interpretation terminal) (terminal-side operation reception processing, terminal-side operation reception step).

The operation reception processing unit 110C (processor 110) of the interpretation support server 100 receives an operation performed by the interpretation terminal 200A (YES in Step S110: operation reception processing, operation reception step). This operation includes designation of a third terminal that is different from the first terminal and the second terminal, the third terminal being permitted to display a result of the hide operation. The classification processing unit 110E determines whether or not the interpretation terminal to be processed has received the input of the interpretation terminal (third terminal different from the first terminal and the second terminal) that is permitted to display the result of the hide operation (Step S142: other terminal result display processing, other terminal result display step). In the above example, the interpretation terminal 200B is determined to be the third terminal.

The other terminal result display processing unit 110F (processor 110) causes the display device 250 of the interpretation terminal 200B (third terminal, other terminal) to display the result of the hide operation in real time (Step S144: other terminal result display processing, other terminal result display step, first result display processing, first result display step), and prohibits the interpretation terminal not designated by engineer A (in this case, the interpretation terminal 200C) from displaying the operation result of the hide operation.

The above-described display of the operation result is also performed in the same manner for the operation by engineer B (the interpretation terminal 200B), and the result of the display operation on the interpretation terminal 200B is displayed on the interpretation terminal 200A. In a case where the operation result is shared among some users in this manner, the interpretation support server 100 can display the operation result in the individual display region of the display device 250.

By sharing the operation results in this manner, the user (in this case, engineer A) can easily and accurately grasp the thoughts and the interpretation results of the other user (engineer B). Such a function can be utilized, for example, in a case where an inexperienced engineer performs interpretation with the support of an experienced engineer. On the other hand, the remaining user (engineer C) can proceed with the interpretation work as usual without being influenced by the thoughts or the interpretation results of the other users. Thereby, all the users can efficiently perform the interpretation according to the situation.

It is preferable that the result of the hide operation is shared among some users in a case where all the users who share the result agree. For example, in the above-described example, it is preferable to perform the above-described processing in a case where engineer A desires to share an operation result with engineer B and engineer B agrees to share the operation result. The interpretation support server 100 can notify engineer B (interpretation terminal 200B) that engineer A desires to share the operation result with engineer B, and can determine that such an agreement has been made in a case where engineer B performs an operation of agreeing to it via the operation unit 260.

Figure 13:
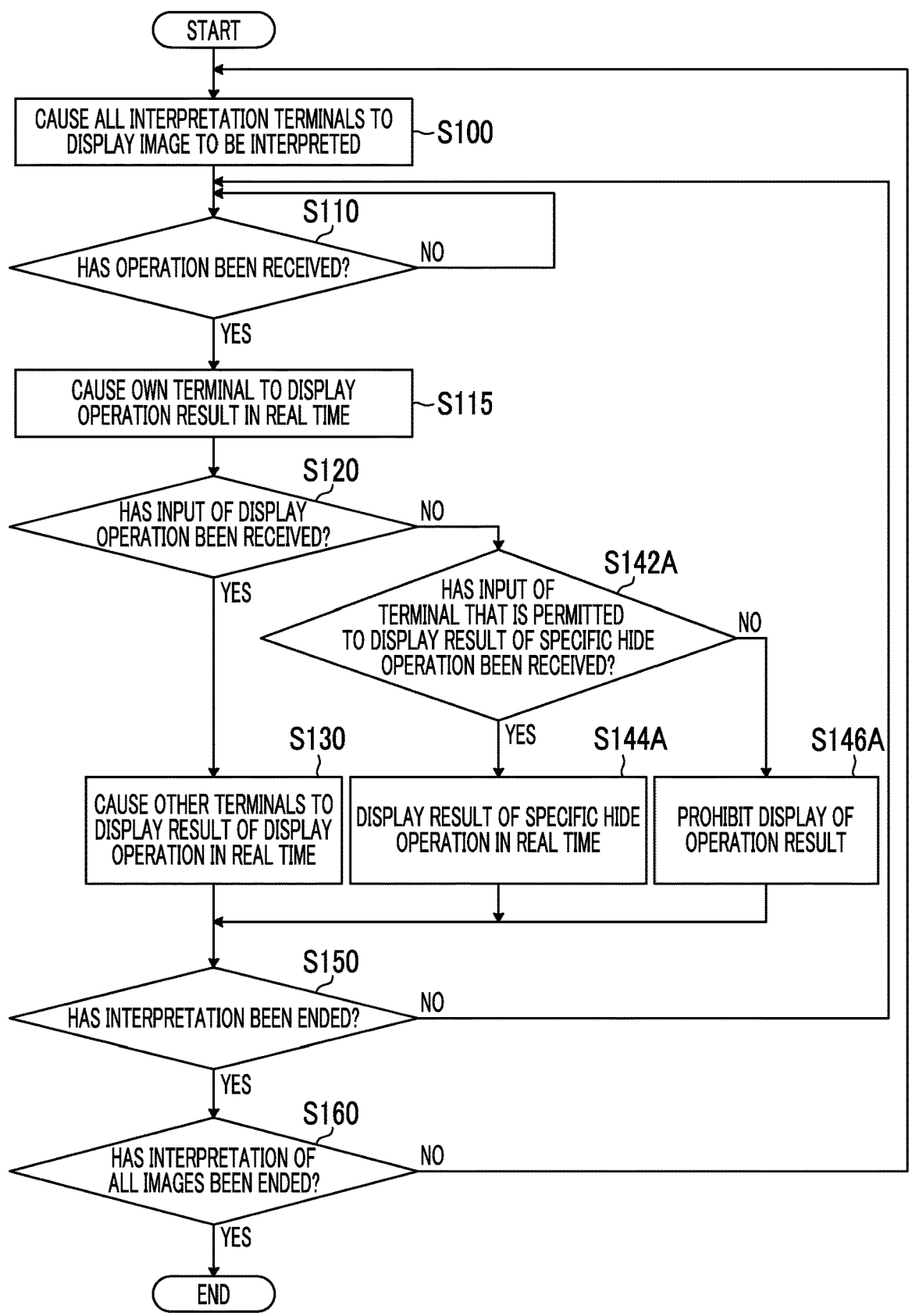
FIG. 13 is still another flowchart showing processing in the interpretation support server.

Instead of or in addition to the aspect of sharing the result of the hide operation among some users as described above, a certain user (for example, the interpretation terminal 200A) may share operation results with another user (for example, the interpretation terminal 200B) for only a designated operation among the hide operations (hereinafter referred to as a "specific hide operation"). For example, a process may be performed such that "the operation result is shared with other users for enlargement/reduction or movement of the image to be interpreted, and the operation result is not shared with other users for changing the brightness of the image to be interpreted. In this case, as shown in FIG. 13, the operation reception processing unit 110C (processor 110) of the interpretation support server 100 receives an operation performed by the interpretation terminal 200A (YES in Step S110: operation reception processing, operation reception step). This operation includes designation of a fourth terminal that is different from the first terminal and the second terminal, the fourth terminal being permitted to display a result of a specific hide operation which is a designated operation among the hide operations. The classification processing unit 110E (processor) determines whether or not the input of the terminal (fourth terminal) that is permitted to display the result of the specific hide operation has been received (Step S142A: classification processing, classification step). That is, the classification processing unit 110E (processor) determines whether or not the hide operation is the specific hide operation (Step S142A: classification processing, classification step), causes another interpretation terminal 200 (another terminal, the fourth terminal that is different from the first terminal and the second terminal) to display a result of the specific hide operation in real time (Step S144A: other terminal result display processing, other terminal result display step), and prohibits the other interpretation terminal 200 from displaying operation results for hide operations other than the specific hide operation (Step S146A: other terminal result display processing, other terminal result display step). For example, the classification processing unit 110E can determine whether or not the input of the terminal that is permitted to display the result of the specific hide operation has been received, that is, whether or not the hide operation is the specific hide operation, based on the operation of engineer A who is the user of the interpretation terminal 200A. In addition, the users (interpretation terminal 200, fourth terminal) who share the result of the specific hide operation may be all other users (for example, engineer B, engineer C, and engineer D in a case where engineer A is focused on), or may be only some users (for example, engineer D (interpretation terminal 200D) in a case where engineer A is focused on).

[Level Setting of User/Interpretation Terminal]

In the first embodiment and the modification example, in a case where a plurality of users perform interpretation, the interpretation support system 10 (interpretation support server 100) may set administrator authority for some users (or interpretation terminals), and receive operations for those users that cannot be performed by other users. For example, it is conceivable to receive operations from a user having administrator authority for operations such as instructions to start and end interpretation and designation of an image to be interpreted.

[Communication Between Interpretation Terminals]

Further, in the first embodiment and the modification example, the processor 110 (communication control unit 110I) and the processor 210 (communication control unit 210D) may communicate with each other between the interpretation terminals.

In a case where a plurality of users perform the interpretation in parallel, the interpretation can be performed more efficiently if communication is possible, and even users at a remote location can easily participate in the interpretation. Such communication can be performed through an image, voice, text, and the like.

[Other Examples of Imaging Apparatus and Image to be Interpreted]

In the first embodiment and modification example described above, a case where a radiation image of an industrial product is used as an image to be interpreted has been described. However, in the present invention, an image captured in a wavelength band of visible light, ultrasound, or the like may be used as the image to be interpreted, in addition to the radiation image.

Further, in the present invention, an image of an object other than an industrial product can be used as an image to be interpreted. Specifically, for example, an image of a building (an example of an object; the image may be a building or a structure) captured in a wavelength band such as visible light, infrared light, or millimeter waves may be used as the image to be interpreted. Here, examples of the "building" include bridges, bridge piers, roads, tunnels, dams, and buildings. The building may be made of concrete. In addition, in the present invention, a medical image of a living body (an example of an object) imaged by an imaging apparatus such as an endoscope apparatus, an ultrasound apparatus, a computed tomography (CT) apparatus, or a magnetic resonance imaging (MRI) apparatus may be used an image to be interpreted. In addition, the interpretation support system may acquire the image to be interpreted from a system such as a hospital information system (HIS) or a radiology information system (RIS).

In addition, in images to be interpreted for buildings or medical images as objects, damage and deformation such as cracks, detachment, and water leakage in buildings, lesions and their candidates in medical images, and regions of interest (ROI: referred to as regions of attention") such as organs and blood vessels can be handled in the same manner as the "defect" in the first embodiment.

In addition, in a case where a plurality of images obtained by performing divisional imaging of the object are used as an image to be interpreted, a combined image obtained by combining these images, for example, a panoramic image, may be used as an image to be interpreted. Depending on the shape and size of the object, the imaging target may be captured in a plurality of times, and in this case, a plurality of images over a wide range may be combined into one image. In addition, in some cases, a plurality of users share and interpret the images over such a wide range. According to the aspects of the present invention, even in such a case, a plurality of users can simultaneously access the same image and perform interpretation efficiently.

Although the embodiment and the modification example of the present invention have been described above, it is needless to say that the present invention is not limited to the aspect described above, and various modifications can be made without departing from the gist of the present invention.

EXPLANATION OF REFERENCES

10: interpretation support system
100: interpretation support server
110: processor
110A: image acquisition unit
110B: image display processing unit
110C: operation reception processing unit
110D: own terminal result display processing unit
110E: classification processing unit
110F: other terminal result display processing unit
110G: collation processing unit
110H: notification processing unit
110I: communication control unit
120: ROM
130: RAM
140: recording device
200: interpretation terminal
200A: interpretation terminal
200B: interpretation terminal
200C: interpretation terminal
200D: interpretation terminal
210: processor
210A: terminal-side image display processing unit
210B: terminal-side operation reception processing unit
210C: terminal-side result display processing unit
210D: communication control unit
220: ROM
230: RAM
240: recording device
250: display device
252A: display device
254A: display device
260: operation unit
300: imaging system
400: database
502A: screen 502B: screen
504A: screen
504B: screen
512A: entire display region
512B: entire display region
514A: individual display region
514B: individual display region
520A: interpretation range
520B: interpretation range
522A: entire display screen
522B: entire display screen
524A: individual display screen
524B: individual display screen
526: region
526A: entire display region
526B: entire display region
528: message
528A: individual display region
528B: individual display region
530A: region
530B: region
530C: region
540A: region
540B: region
542A: region
542B: region
550A: entire display region
552A: individual display region
560A: screen
562: entire display region
562A: entire display region
564A: individual display region
566A: region
566B: region
566C: region
566D: region
600: object
NW: network
S100 to S160: each step of interpretation support method
S142A, S144A, S146A: each step of interpretation support method

What is claimed is:

1. An interpretation support server comprising a processor,
wherein the processor is configured to execute:
image display processing for causing a first terminal connected to the interpretation support server and a second terminal different from the first terminal to display an image to be interpreted for an object;
operation reception processing for receiving operations performed on the displayed image to be interpreted at the first terminal and the second terminal;
own terminal result display processing for causing the first terminal to display a result of processing based on the operation received from the first terminal in real time and causing the second terminal to display a result of processing based on the operation received from the second terminal in real time;
classification processing for classifying the operation received from the first terminal into a display operation and a hide operation; and
other terminal result display processing for causing the second terminal to display a result of performed display operation in real time in a case where the display operation is performed at the first terminal, and prohibiting the second terminal from displaying a result of performed hide operation in a case where the hide operation is performed at the first terminal.

2. The interpretation support server according to claim 1, wherein the processor is configured to, in the classification processing:
classify, as the display operation, an operation in which users of the first terminal and the second terminal input information indicating an interpretation result of the image to be interpreted; and
classify, as the hide operation, an operation in which the user of the first terminal inputs information regarding processing of the image to be interpreted.

3. The interpretation support server according to claim 2, wherein the processor is configured to, in the classification processing:
receive, as the information indicating the interpretation result, at least one of the number, position, type, degree, or reason for determining the degree of defects in the image to be interpreted; and
receive, as the information regarding processing of the image to be interpreted, at least one of an enlarging or reducing operation, a moving operation, a rotating operation, a transforming operation, an operation of changing a gradation, an operation of setting an interpretation range, an operation of designating a defect, or an operation of setting interpretation content for the image to be interpreted.

4. The interpretation support server according to claim 3, wherein the processor is configured to:
in the classification processing, receive, as the information regarding processing of the image to be interpreted, the operation of setting the interpretation range for the image to be interpreted; and
perform notification processing for notifying a user of a confirmation result as to whether or not a region in which the object is shown in the image to be interpreted is entirely covered by the set interpretation range.

5. The interpretation support server according to claim 2, wherein the processor is configured to, in the other terminal result display processing, cause the second terminal to identify and display the information indicating the interpretation result in association with a fact that the interpretation result has been input from the first terminal.

6. The interpretation support server according to claim 1, wherein the processor is configured to:
in the operation reception processing, receive designation of a third terminal, the third terminal being different from the first terminal and the second terminal and being permitted to display a result of the hide operation;
in the image display processing, cause the third terminal to display the image to be interpreted; and
in the other terminal result display processing, cause the third terminal to display the result of the hide operation in real time.

7. The interpretation support server according to claim 1, wherein the processor is configured to:
in the operation reception processing, receive designation of a fourth terminal, the fourth terminal being different from the first terminal and the second terminal and being permitted to display a result of a specific hide operation which is a designated operation among the hide operations;
in the image display processing, cause the fourth terminal to display the image to be interpreted; and in the other terminal result display processing, cause the fourth terminal to display the result of the specific hide operation in real time.

8. The interpretation support server according to claim 1, wherein the processor is configured to cause the first terminal and the second terminal to display, as the image to be interpreted, any one of an image of a building, an image of an industrial product, or a medical image of a living body.

9. An interpretation support system comprising:

an interpretation support server including a processor;

a first terminal that is connected to the interpretation support server and displays an image to be interpreted; and a second terminal that is connected to the interpretation support server and displays the image to be interpreted, the second terminal being different from the first terminal, wherein the processor is configured to execute:
- image display processing for causing the first terminal connected to the interpretation support server and the second terminal different from the first terminal to display the image to be interpreted for an object;
- operation reception processing for receiving operations performed on the displayed image to be interpreted at the first terminal and the second terminal;
- own terminal result display processing for causing the first terminal to display a result of processing based on the operation received from the first terminal in real time and causing the second terminal to display a result of processing based on the operation received from the second terminal in real time;
- classification processing for classifying the operation received from the first terminal into a display operation and a hide operation; and
- other terminal result display processing for causing the second terminal to display a result of performed display operation in real time in a case where the display operation is performed at the first terminal, and prohibiting the second terminal from displaying a result of performed hide operation in a case where the hide operation is performed at the first terminal.

10. An interpretation support method executed by an interpretation support server, the interpretation support method comprising:

an image display step of causing a first terminal connected to the interpretation support server and a second terminal different from the first terminal to display an image to be interpreted for an object;

an operation reception step of receiving operations performed on the displayed image to be interpreted at the first terminal and the second terminal;

an own terminal result display step of causing the first terminal to display a result of processing based on the operation received from the first terminal in real time and causing the second terminal to display a result of processing based on the operation received from the second terminal in real time;

a classification step of classifying the operation received from the first terminal into a display operation and a hide operation; and an other terminal result display step of causing the second terminal to display a result of performed display operation in real time in a case where the display operation is performed at the first terminal, and prohibiting the second terminal from displaying a result of performed hide operation in a case where the hide operation is performed at the first terminal.

11. A non-transitory, computer-readable tangible recording medium on which a program for causing, when read by a computer, the computer to execute the interpretation support method according to claim 10 is recorded.

12. An interpretation terminal connected to an interpretation support server, the interpretation terminal comprising a processor, wherein the processor is configured to execute:
- terminal-side image display processing for displaying an image to be interpreted for an object under control of the interpretation support server;
- terminal-side operation reception processing for receiving an operation of a user on the image to be interpreted; and
- terminal-side result display processing for displaying a result processed by the interpretation support server according to a classification result in the interpretation support server as to whether the received operation is a display operation that permits display of an operation result on another interpretation terminal connected to the interpretation support server or the received operation is a hide operation that prohibits display of the operation result on the other interpretation terminal, the terminal-side result display processing performing first result display processing for displaying a result of the display operation received by the interpretation terminal and a result of the hide operation received by the interpretation terminal or second result display processing for displaying a result of the display operation received by the other interpretation terminal.

* * * * *